(12) United States Patent
Keady

(10) Patent No.: US 9,039,637 B2
(45) Date of Patent: May 26, 2015

(54) FLEXIBLE CYTOLOGY COIL

(71) Applicant: Cook Medical Technologies LLC, Bloomington, IN (US)

(72) Inventor: Fionan Keady, Glenamaddy (IE)

(73) Assignee: Cook Medical Technologies LLC, Bloomington, IN (US)

( * ) Notice: Subject to any disclaimer, the term of this patent is extended or adjusted under 35 U.S.C. 154(b) by 154 days.

(21) Appl. No.: 13/800,170

(22) Filed: Mar. 13, 2013

(65) Prior Publication Data

US 2014/0276204 A1 Sep. 18, 2014

(51) Int. Cl.
*A61B 5/00* (2006.01)
*A61B 5/053* (2006.01)

(52) U.S. Cl.
CPC ...................... *A61B 5/053* (2013.01)

(58) Field of Classification Search
CPC .................. A61B 10/02; A61B 2010/0216
USPC .................................. 600/569–572
See application file for complete search history.

(56) References Cited

U.S. PATENT DOCUMENTS

| | | | |
|---|---|---|---|
| 2,839,049 A * | 6/1958 | MacLean | 600/569 |
| 3,996,938 A | 12/1976 | Clark, III | |
| 4,465,072 A | 8/1984 | Taheri | |
| D300,060 S | 2/1989 | Molgaard-Nielsen | |
| 4,927,412 A | 5/1990 | Menasche | |
| 4,958,621 A | 9/1990 | Topel et al. | |
| 4,989,614 A | 2/1991 | Dejter, Jr. et al. | |
| 5,037,379 A | 8/1991 | Clayman et al. | |
| 5,048,538 A | 9/1991 | Terwilliger et al. | |
| 5,060,658 A | 10/1991 | Dejter, Jr. et al. | |
| 5,083,572 A | 1/1992 | Pokorny | |
| 5,146,921 A | 9/1992 | Terwilliger et al. | |
| 5,249,583 A | 10/1993 | Mallaby | |
| 5,253,652 A | 10/1993 | Fast | |
| 5,287,857 A | 2/1994 | Mann | |
| 5,423,745 A | 6/1995 | Todd et al. | |
| D360,260 S | 7/1995 | Brandt | |
| 5,488,958 A | 2/1996 | Topel et al. | |
| D369,857 S | 5/1996 | Booth et al. | |
| 5,535,756 A | 7/1996 | Parasher | |
| 5,702,413 A | 12/1997 | Lafontaine | |
| 5,713,369 A | 2/1998 | Tao et al. | |
| 5,749,883 A | 5/1998 | Halpern | |
| 5,797,953 A | 8/1998 | Tekulve | |
| 6,258,044 B1 * | 7/2001 | Lonky et al. | 600/569 |
| 6,346,086 B1 * | 2/2002 | Maksem et al. | 600/569 |
| 6,468,228 B1 | 10/2002 | Topel et al. | |
| 6,685,718 B1 | 2/2004 | Wzygala et al. | |
| 6,800,083 B2 | 10/2004 | Hiblar et al. | |
| 7,252,674 B2 | 8/2007 | Wyzgala et al. | |
| 7,641,620 B2 | 1/2010 | Wingler | |
| 7,878,983 B2 | 2/2011 | Karpiel | |
| 8,034,022 B2 | 10/2011 | Boatman | |
| 8,052,613 B2 * | 11/2011 | Assell et al. | 600/562 |

(Continued)

*Primary Examiner* — Max Hindenburg
(74) *Attorney, Agent, or Firm* — Brinks Gilson & Lione

(57) ABSTRACT

A medical device for collecting cells includes a delivery tube having a flexible wire disposed within a lumen of the tube. The flexible wire includes a rigid proximal portion and a flexible distal portion. The flexible distal portion includes a cell collecting portion that can be advanced out of the needle and into a body cavity. The flexible nature of the wire will allow it to generally fill the body cavity to increase the contacted surface area and the amount of cells that are collected. The wire can then be retracted back into the needle for removal from the patient's body.

29 Claims, 3 Drawing Sheets

(56) References Cited

U.S. PATENT DOCUMENTS

| | | |
|---|---|---|
| 8,057,496 B2 | 11/2011 | Fischer, Jr. |
| 8,070,691 B2 | 12/2011 | Desilets et al. |
| 8,100,881 B2 | 1/2012 | Hoffa |
| 8,123,769 B2 | 2/2012 | Osborne |
| 8,246,641 B2 | 8/2012 | Osborne et al. |

* cited by examiner

FLEXIBLE CYTOLOGY COIL

BACKGROUND

The present invention relates to cell collection devices. More particularly, the invention relates to a cell collection device having a flexible wire for collecting cells.

Cell collecting devices, or cytology devices, are well known in the art. A traditional cell collection device can be in the form of a cytology brush. A cytology brush can generally be used by being inserted into a body cavity of a patient, where the brush can contact the body cavity wall to collect cells. Cytology brushes are generally elongate, and include a distal end having a plurality of metal or plastic bristles extending radially outward. The brush can be in the form of a metallic coiled wire, and the bristles can be disposed between the coils. The coiled nature of the brush allows it to generally bend and navigate various tortuous body vessels. Additionally, the coils allow the brush to retain its pushability for delivering the brush through the anatomy.

However, the brushes can be ineffective in collecting a sufficient number of cells and can lead to irritation or bleeding during the cell collection process. The distal end of the brush is generally narrow and has a limited surface area for collecting cells. Moreover, the body vessels for which cell collection is desired can vary greatly from patient to patient. To collect the cells, the brush is inserted into the cavity and brushed against the cavity wall repeatedly, with pressure applied to the wall by the brush so that bristles contact the cavity. This brushing can often lead to bleeding, while collecting only a limited number of desired cells from a limited and inconsistent area of the cavity.

SUMMARY

A medical device for collecting cells is provided, the device comprising: an elongate tube having proximal and distal portions and a lumen extending therebetween; a distal opening of the tube disposed at the distal portion; an elongate wire extending through the tube lumen, the wire comprising a generally rigid proximal portion and a generally flexible distal portion including a cell collecting portion for collecting cells from a body cavity; wherein the wire proximal portion is configured for being pushed distally through the tube lumen while being at least partially retained within the tube lumen; and wherein the flexible distal portion of the wire is operable in a cell collecting configuration where it is pushed out of the distal opening of the tube and into a body cavity to folds over itself in a random tortuous pattern to form a random, overlapping, tortuous path in response to the proximal portion being pushed.

In another form, the cell collecting portion includes an absorbable component. In another form, wherein the flexible distal portion comprises a coiled wire.

In another form, the flexible distal portion comprises a thin solid wire that is thinner than the proximal portion.

In another form, the flexible distal portion comprises a braided wire.

In another form, the flexible distal portion is between ⅛ and ½ of the total length of the wire.

In another form, the absorbable component comprises cotton.

In another form, the cell collecting portion includes a plurality of micro-protrusions.

In another form, the cell collecting portion includes an absorbable component disposed between the coils of the coiled wire.

In another form, the cell collecting portion comprises an abraded surface of the flexible distal portion.

In another form, the flexible distal portion has a modulus of elasticity that is lower than the proximal portion of the wire so that the distal portion is more flexible than the proximal portion.

In another form, the braided wire includes an absorbable component intertwined with individual strands of the braided wire.

In another form, the micro-protrusions are generally evenly spaced about the cell collecting portion.

In another form, a system for collecting cells from a body cavity is provided, the system comprising: a tubular delivery device having a proximal portion and a distal portion, a lumen extending therebetween, and a distal opening; a flexible wire disposed within the tubular delivery device, the flexible wire having a distal end disposed proximally of the distal opening when the wire is in a delivery configuration and extended distally from the bevel portion when the wire is in an exposed configuration; and wherein the flexible wire is folded over itself and bent in a random and tortuous pattern to form a random, overlapping, tortuous path conforming to the general shape of the body cavity into which it is inserted when in the exposed configuration.

In another form, the wire includes a proximal portion that remains within the delivery device when the wire is in the exposed configuration and the distal portion forms the random, overlapping, tortuous path within the body cavity.

In another form, the delivery device comprises a rigid needle having a beveled end. In another form, the distal portion of the wire includes an absorbable component.

In another form, the absorbable component comprises an absorbable coating.

In another form, the absorbable component comprises an absorbable sleeve.

In another form, the absorbable component includes micro-protrusions.

In another form, a method for collecting cells from a body cavity is provided, the method comprising: inserting a cell collecting device into a body cavity, the cell collecting device comprising: a tubular delivery device having a proximal portion, a distal portion, a lumen extending therebetween, and an opening at the distal portion; a flexible wire having a cell collecting portion disposed at a distal portion thereof, the flexible wire being housed within the delivery device lumen when the wire is in a delivery configuration and extending from the delivery device when the wire is in a cell collecting configuration; translating the flexible wire distally along the lumen; extending the cell collecting portion from the delivery device opening; contacting a surface of the body cavity with flexible wire; deforming the flexible wire to contact and abrade additional areas of the body cavity surface; collecting cells from the body cavity surface; retracting the wire into the delivery device; and removing the delivery device and wire having the cells.

In another form, the method further comprises folding and bending the flexible wire in a random and tortuous pattern to form a random, overlapping, tortuous path conforming to the shape of the body cavity.

In another form, the flexible wire comprises a generally rigid proximal portion and a flexible distal portion.

In another form, extending the cell collecting portion comprises pushing the generally rigid proximal portion.

In another form, the cell collecting portion comprises an absorbable portion.

In another form, the cell collecting portion includes a plurality of micro-protrusions.

DETAILED DESCRIPTION

Figure 1:
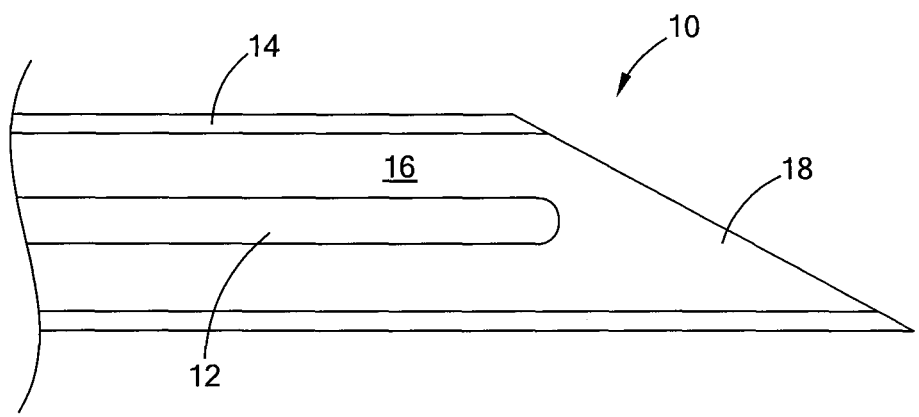
FIG. 1 is a schematic view of a cell collection device having a delivery tube and a wire.

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Referring now to the drawings, FIGS. 1-12 illustrate a cell collection system 10 including a flexible wire 12 for collecting cells from a body cavity and a needle 14 for delivering the wire 12 to the target area for cell collection. The flexible wire 12 is housed within the needle 14 in a delivery configuration for insertion into the target area. The wire 12 is configured for being extended out of the needle 14 at the target area, where the flexible nature of the needle 14 can cause it to bend and twist to substantially fill the body cavity to collect a high number of cells.

Figure 2:
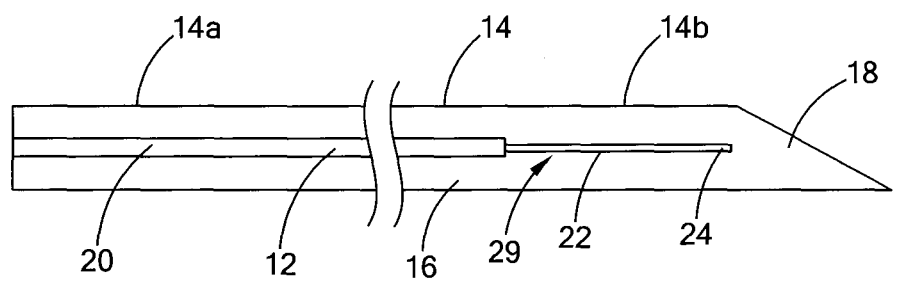
FIG. 2 is a schematic view of the device showing a proximal and distal portion of the wire.

With reference to FIGS. 1 and 2, the needle 14 can be a traditional needle used for delivery of traditional cytology brushes. The needle 14 includes a proximal portion 14a and a distal portion 14b. The needle 14 has a generally tubular form defining a lumen 16 extending through the needle 14. The distal end 14b includes a sharp bevel portion 18. The bevel portion 18 is configured for being inserted into a body cavity, cyst, or the like, and can puncture the surface of the body cavity or cyst to provide access. However, it will be appreciated that the needle 14 can be in other tubular forms known in the art, such as a flexible tube having a blunt end where puncturing is not necessary. For the purposes of discussion, the needle 14 having the bevel portion 18 will be described.

The flexible wire 12 can be in the form of a single wire, or it can include a separate proximal portion 20 and a distal portion 22. The distal portion 22 is preferably between ⅛ and ½ of the overall length of the wire 12, most preferably approximately ⅓ of the length of the wire 12. In one form, the overall length of the wire 12 can be 1000 mm and the distal portion can be 333 mm. Of course, other relative sizes between the proximal portion 20 and distal portion 22 could also be used, as well as other overall lengths of the wire 12 depending on where and how the wire 12 is desired to be used. The distal portion 22 can be highly flexible relative to the proximal portion 20, so that the proximal portion 20 can be pushable through the needle 14, with the highly flexible distal portion 22 being inserted into the body cavity. The term "flexible" or "generally flexible" as used herein means a wire that can easily flex greater than 360 degrees along a path to be able to fold over itself in a random and tortuous pattern to conform to the shape of the body cavity in which it is inserted.

As mentioned above, the wire 12 can be a single wire that retains sufficient pushability while remaining flexible enough to bend and fill a body cavity. However, for the purposes of discussion, the wire 12 will be generally described as having the highly flexible distal portion 22 and the more rigid proximal portion 20. In one form, the proximal portion 20 can be stiffened by providing a stiffening layer or sheath (not shown) around the wire 12 at the proximal portion 20 with the distal portion 22 remaining free from stiffening layers, or fewer stiffening layers can be used at the distal portion 22 relative to the proximal portion 20, thereby making the proximal portion 20 more rigid and pushable and the distal portion 22 more flexible than the proximal portion 20. In another form, the proximal portion 20 and distal portion 22 can be distinct portions coupled to each other.

The distal portion 22 can be made from various materials and constructions. In one form, the distal portion 22 is in the form of a solid wire 24, as shown in FIG. 2. The solid wire 24 can have a generally circular cross-section or other cross-sectional shape. The solid wire 24 can be sized so as to be highly flexible so that it can easily fold over to fill the body cavity where cell collection is desired. The solid wire 24 can be so flexible that it may not retain sufficient pushability; however, the proximal portion 20 can be substantially rigid to provide the necessary pushability to force the solid wire 24 out of the needle 14 and into the body cavity. The solid wire 24 can be a metal or polymer, such as Nitinol, stainless steel, nylon, PEBAX, PET, silicon, hydrogels, PEEK, polyurethane, polyester, or the like.

Figure 3:
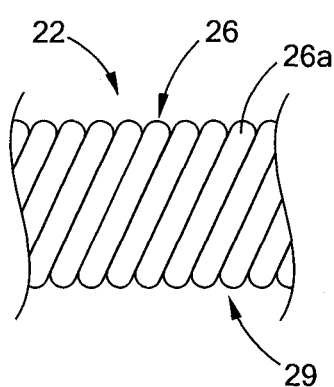
FIG. 3 is a partial side view of a coiled wire embodiment of the wire.

With reference to FIG. 3, in another form, the distal portion 22 could be in the form of a coiled wire 26. Traditional coiled wire construction is known in the art. One type of coiled wire construction is disclosed in U.S. Pat. No. 5,797,953, which is hereby incorporated by reference in its entirety. The coiled wire 26 can be coiled to define multiple coils 26a that create a generally straight shape, while remaining highly flexible to conform to the body cavity in which it is inserted to collect the cells. The coiled wire 26 can be a metal or polymer, such as Nitinol, stainless steel, nylon, PEBAX, PET, silicon, or the like. A smaller wire thickness will generally have greater flexibility but lower strength, and a larger wire thickness will generally have lower flexibility but greater strength; therefore, the specific wire sizing can be selected based on the needs of the user.

Figure 4:
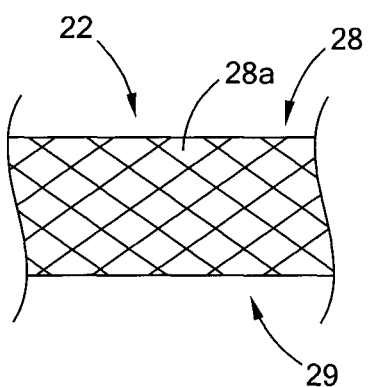
FIG. 4 is a partial side view of a braided wire embodiment of the wire.

With reference to FIG. 4, in another form, the distal portion 22 could be in the form of a braided wire 28. The braided wire 28 can be constructed using a plurality of woven strands of material to create the braid using known methods. The braided wire 28 can be constructed from multiple strands 28a using one or more metal or polymer materials such as Nitinol, stainless steel, nylon, PEBAX, PET, silicon, or the like. For example, some of the strands 28a can be one material with the other strands being a different material, or the strands 28a can be the same material. A smaller wire thickness will generally have greater flexibility but lower strength, and a larger wire thickness will generally have lower flexibility but greater strength; therefore, the specific wire sizing can be selected based on the needs of the user.

The distal portion 22 can also include a cell collecting portion 29 in the form of an absorbable portion 30 comprising at least a portion of the distal portion 22. Put another way, the various distal portions 22 described above could be made from an absorbable material, or an absorbable material could be included with a non-absorbable material. In another form, the distal portion 22 itself could be the cell collecting portion 29, where the coils 26a of the coiled wire 26 or the strands 28a of the braided wire 28 can collect the cells (FIGS. 2-4). The absorbable material comprising the absorbable portion 30 can be one of many possible materials with a low surface wettability capable of absorbing fluids. For example, the absorbable portion 30 could be made from cotton, PET, nylon, open or closed cell foam, Dacron, or the like.

Figure 5:
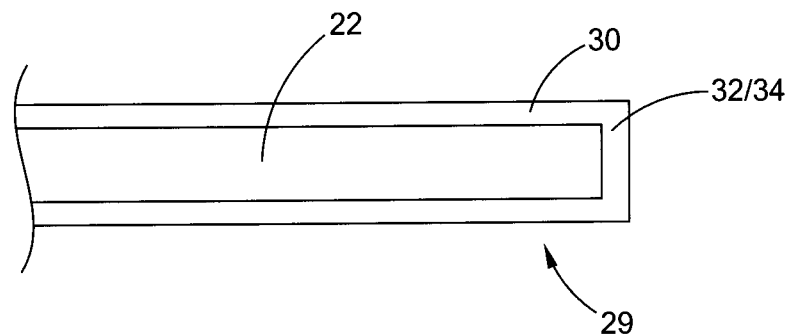
FIG. 5 is a schematic view of an absorbable portion of the wire.

With reference to FIG. 5, the absorbable portion 30 could be in the form of a coating 32 applied to one of the distal portions 22 described above. The coating 32 can cover the entire distal portion 22 or a portion of the distal portion 22. The coating 32 can be applied after the distal portion 22 is fully constructed, as in the case of the coiled wire 26 or braided wire 28, or it can be applied to the material of the distal portion 22 prior to the coiling or braiding.

In another form, the absorbable portion 30 can be in the form of a sleeve 34 attached to the distal portion 22. The sleeve 34 can cover the entire distal portion 22 or a portion of the distal portion 22. The sleeve 34 can be flexible enough to bend along with the distal portion 22 to fill the desired body cavity.

Figure 7:
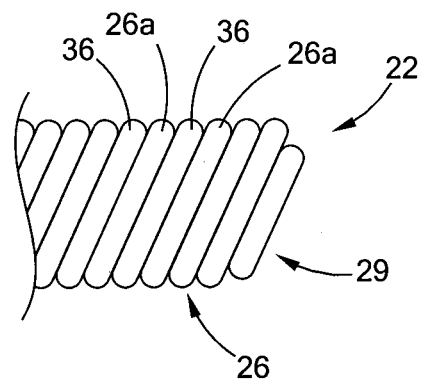
FIG. 7 is a partial side view of the coiled wire embodiment having an absorbable portion.
Figure 6:
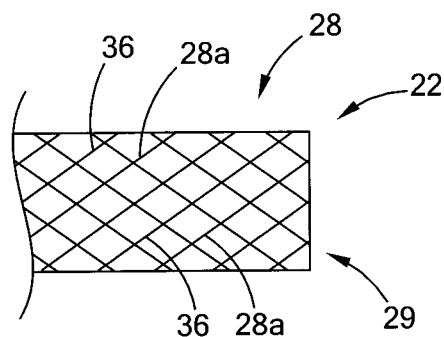
FIG. 6 is a partial side view of the braided wire embodiment having an absorbable portion.
Figure 8:
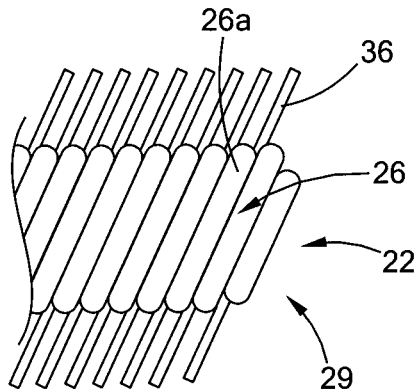
FIG. 8 is a partial side view of the coiled wire embodiment having an absorbable portion extending outwardly from the wire.

With reference to FIGS. 6-8, in another form, the absorbable portion 30 can be in the form of an absorbable member 36 interwoven with the wire of the distal portion 22. In the case of the braided wire 28, the absorbable member 36 can be in the form of strands that are interwoven with the other strands 28a to form the braided wire 28 (FIG. 6). In the case of the coiled wire 26, the absorbable member 36 can be in the form of coils that are coiled with the coils 26a to form the coiled wire 26 (FIG. 7) or the absorbable member 36 can extend radially outward and be held between the coils 26a of the coiled wire 26 (FIG. 8), similar to the bristles of a traditional cytology brush.

Figure 9:
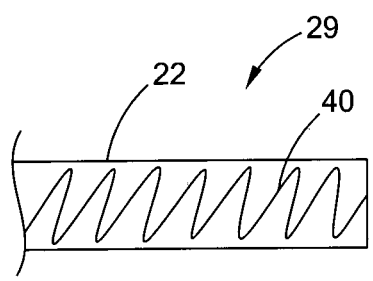
FIG. 9 is a schematic view of the wire having a roughened portion.

With reference to FIG. 9, alternatively, or in addition to the absorbable portion 30, the cell collecting portion 29 can be in the form of a roughened portion 40 that extends along the entire distal portion 22 or a portion of the distal portion 22. The roughened portion 40 can be constructed using chemical etching, mechanical etching, sand blasting, or other abrasion techniques. The roughened portion 40 can assist in collecting cells when the distal portion 22 is inserted into the desired body cavity. In one form, the roughened portion 40 can be constructed as a sleeve of material that surrounds a portion of the distal portion 22. In another form, individual strands 28a of the braided wire 28 or coils 26a of the coiled wire 26 could be roughened to create the roughened portion 40.

Figure 10:
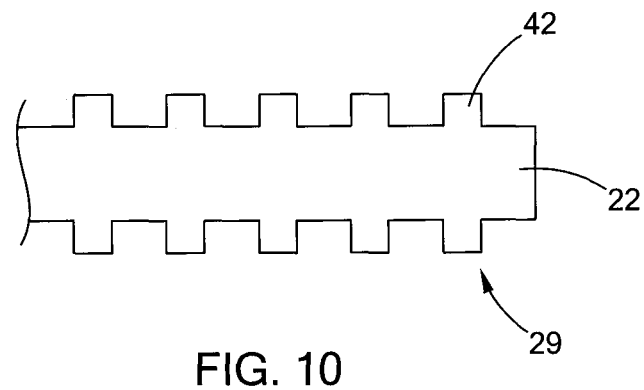
FIG. 10 is a schematic view of the wire having micro-protrusions.

With reference to FIG. 10, the cell collecting portion 29 can be in the form of a plurality of micro-protrusions 42. The micro-protrusions 42 can be made for example from a silicon mold and can be flexible. The micro-protrusions 42 increase the surface area of the distal portion 22 for increasing the number of cells that can be collected. The protrusions 42 can be integrally formed with the material of the distal portion 22 or the absorbable component 30. The protrusions 42 can be spaced evenly about the distal portion 22 or can be disposed in groups such that the groups of protrusions 42 are spaced apart evenly, or at varying distances. It will be appreciated that various spacing and numbers of protrusions 42 can be used depending on the needs of the user. Generally, an increased number of protrusions 42 will increase the amount of cells collected, but reducing the number of protrusions 42 could also be beneficial in some instances, such as a desire to increase the ability of the protrusions to flex into adjacent space.

The above described embodiments of the cell collecting portion 29, such as the absorbable portion 30, the roughed portion 40, the micro-protrusions 42, or the distal portion 22 itself can be used alone or in combination with each other to increase the ability of the distal portion 22 to collect cells. It will be appreciated that the various types of distal portions 22 and manners of increasing their cell collecting ability can lead to myriad possibilities for constructing the distal portion 22.

Having described the general structure of the device 10 above, the use of the device 10 will now be described.

Figure 11:
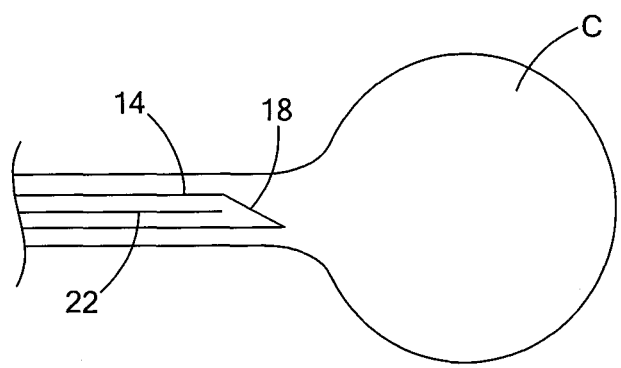
FIG. 11 is a schematic view of the wire and delivery tube in a delivery configuration and inserted toward a body cavity.

With reference to FIG. 11, the wire 12 is disposed within the needle 14 along the length of the needle 14. The distal portion 22 is positioned proximally of the bevel portion 18 so that the distal portion 22 remains housed within the needle 14. In this position, the wire 12 is a delivery configuration.

The needle 14, housing the wire 12, is inserted into the desired body cavity C where cell collection is anticipated by the user in a manner known in the art. In the event the body cavity needs to be punctured, such as in the case of a cyst (or the like), the bevel portion 18 of the needle 14 can puncture the surface of the cyst to gain entry for the distal portion 14b of the needle 14 into the cyst cavity. In the event that puncturing is not necessary, the needle 14 can merely be tracked through the body toward the desired body cavity C or replaced with a guiding catheter or other tubular delivery device.

Figure 12:
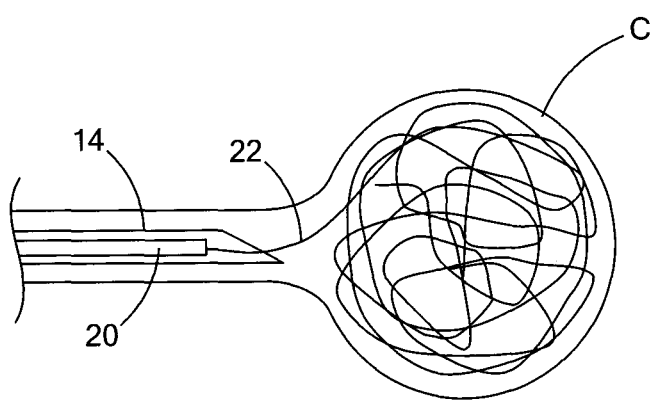
FIG. 12 is a schematic view of the wire in a cell collecting configuration within the body cavity.

With reference to FIG. 12, once the distal portion 14b adjacent the body cavity C for which cell collection is desired, the wire 12 can be inserted into the body cavity C. The proximal portion 20 of the wire 12, having sufficient pushability, can be continuously pushed along and through the lumen 16 of the needle 14. The distal portion 22 will be pushed along by the proximal portion 20, causing the distal portion 22 to emerge from the distal portion 14b of the needle. The wire 12 will be continuously fed out of the needle 14 and into the body cavity C so that the wire 12 is in the cell collecting configuration.

As the wire 12 is inserted into the body cavity C, the highly flexible nature of the distal portion 22 will cause the distal portion 22 to bend and flex to substantially fill the body cavity C. That is, it folds over itself to form a "random, overlapping, tortuous path," i.e. a random or tortuous path that conforms to the space of the cavity C. By filling the body cavity with the distal portion 22, the inner surface of the body cavity C will be substantially covered, thereby increasing the contact area between the body cavity C and the distal portion 22. This procedure is generally the same regardless of the material or configuration of the distal portion 22 that is used. This increased contact area increases the number of cells that can be collected relative to traditional brushing or scraping techniques, which can be unreliable for collecting cells. As more wire 12 is fed into the cavity C, the wire 12 will contact and rub the surface of the surface of the cavity to collect cells through abrasion. The surface of the cavity C, when contacted by the advancing wire 12, will cause the wire 12 to bend and flex in the random and tortuous manner described above to form the "random, overlapping, tortuous path."

The distal portion 22 will remain in the body cavity C only temporarily for a short period of time (enough time for cells to be collected or absorbed by the distal portion). After filling the body cavity with the distal portion 22 and collecting the cells on the distal portion 22, the wire 22 can be retracted back into the needle 14. The proximal portion 20 of the wire 12 can be retracted, thereby pulling the distal portion 22 back into the needle. The highly flexible nature of the distal portion 22 will allow it to be easily pulled back into the needle. The collected cells will tend to stick to the wire 12 and/or absorbable portion 30 of the wire 12.

With the distal portion 22 of the wire 12 housed in the needle 14 once again (similar to the delivery configuration shown in FIG. 11), the needle 14 can be removed from the body, where the wire 12 can subsequently be removed from the needle 14 and the cells collected on the wire 12 can be processed and investigated by known methods.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A medical device for collecting cells from a cyst cavity, the device comprising:
    an elongate tube having proximal and distal portions and a lumen extending therebetween;
    a distal opening of the tube disposed at the distal portion;
    an elongate wire extending through the tube lumen, the wire comprising a generally rigid proximal portion and a generally flexible distal portion including a cell collecting portion for collecting cells from the cyst cavity;
    wherein the wire proximal portion is configured for being pushed distally through the tube lumen while being at least partially retained within the tube lumen; and
    wherein the flexible distal portion of the wire is operable in a cell collecting configuration where it is pushed out of the distal opening of the tube and into the cyst cavity to fold over itself in a random tortuous pattern to form a random, tortuous, overlapping path in response to the proximal portion being pushed;
    wherein the flexible distal portion has a length and flexibility suitable to fold over itself multiple times and to fill the cyst cavity.

2. The medical device of claim 1, wherein the cell collecting portion includes an absorbable component.

3. The medical device of claim 1, wherein the flexible distal portion comprises a coiled wire.

4. The medical device of claim 1, wherein the flexible distal portion comprises a thin solid wire that is thinner than the proximal portion.

5. The medical device of claim 1, wherein the flexible distal portion comprises a braided wire.

6. The medical device of claim 1, wherein the flexible distal portion is between ⅛ and ½ of the total length of the wire.

7. The medical device of claim 2, wherein the absorbable component comprises cotton.

8. The medical device of claim 1, wherein the cell collecting portion includes a plurality of micro-protrusions.

9. The medical device of claim 3, wherein the cell collecting portion includes an absorbable component disposed between the coils of the coiled wire.

10. The medical device of claim 1, wherein the cell collecting portion comprises an abraded surface of the flexible distal portion.

11. The medical device of claim 1, wherein the flexible distal portion has a modulus of elasticity that is lower than the proximal portion of the wire so that the distal portion is more flexible than the proximal portion.

12. The medical device of claim 5, wherein the braided wire includes an absorbable component intertwined with individual strands of the braided wire.

13. The medical device of claim 8, wherein the micro-protrusions are generally evenly spaced about the cell collecting portion.

14. A system for collecting cells from a bodily cavity, the system comprising:
    a tubular delivery device having a proximal portion and a distal portion, a lumen extending therebetween, and a distal opening;
    a flexible wire disposed within the tubular delivery device, the flexible wire having a distal portion with a distal end disposed proximally of the distal opening when the wire is in a delivery configuration and extended distally from the distal opening when the wire is in an exposed configuration; and
    wherein the flexible wire is folded over itself and bent in a random and tortuous pattern to form a random, overlapping, tortuous path conforming to the general shape of the bodily cavity into which it is inserted when in the exposed configuration;
    wherein the distal portion is a single wire in both the delivery configuration and the exposed configuration.

15. The system of claim 14, wherein the wire includes a proximal portion that remains within the delivery device when the wire is in the exposed configuration and the distal portion forms the random, overlapping, tortuous path within the bodily cavity.

16. The system of claim 14, wherein the delivery device comprises a rigid needle having a beveled end.

17. The system of claim 14, wherein the distal portion of the wire includes an absorbable component.

18. The system of claim 17, wherein the absorbable component comprises an absorbable coating.

19. The system of claim 17, wherein the absorbable component comprises an absorbable sleeve.

20. The system of claim 17, wherein the absorbable component includes micro-protrusions.

21. A method for collecting cells from a cyst cavity, the method comprising:
    inserting a cell collecting device into a cyst cavity, the cell collecting device comprising:
        a tubular delivery device having a proximal portion, a distal portion, a lumen extending therebetween, and an opening at the distal portion;
        a flexible wire having a cell collecting portion disposed at a distal portion thereof, the flexible wire being housed within the delivery device lumen when the wire is in a delivery configuration and extending from the delivery device when the wire is in a cell collecting configuration, wherein the distal portion has a length and flexibility suitable to fold over itself multiple times and to fill the cyst cavity;
    translating the flexible wire distally along the lumen;
    extending the distal portion from the delivery device opening;
    contacting a surface of the cyst cavity with the flexible wire;
    deforming the flexible wire to contact and abrade additional areas of the cyst cavity surface;

folding the distal portion over itself multiple times and filling the cyst cavity in response to contacting the surface of the cyst cavity;
collecting cells from the cyst cavity surface;
retracting the wire into the delivery device; and
removing the delivery device and wire having the cells.

22. The method of claim 21 further comprising folding and bending the flexible wire in a random and tortuous pattern to form a random, overlapping, tortuous path conforming to the shape of the cyst cavity.

23. The method of claim 21, wherein the flexible wire comprises a generally rigid proximal portion and a flexible distal portion.

24. The method of claim 23, wherein extending the cell collecting portion comprises pushing the generally rigid proximal portion.

25. The method of claim 21, wherein the cell collecting portion comprises an absorbable portion.

26. The method of claim 21, wherein the cell collecting portion includes a plurality of micro-protrusions.

27. The medical device of claim 1, wherein the flexible distal portion is about ⅓ of the total length of the wire.

28. The medical device of claim 1, wherein the flexible distal portion is about 333 mm in length.

29. The medical device of claim 1, wherein the flexible distal portion includes at least one wire sized and structured relative to the cyst cavity to fold over itself multiple times as it is pushed into the cyst cavity to form a tortuous path that conforms to the cyst cavity and fills the cyst cavity.

* * * * *